(12) United States Patent
Martello

(10) Patent No.: US 7,163,540 B2
(45) Date of Patent: *Jan. 16, 2007

(54) SOFT TISSUE SECURING ANCHOR

(76) Inventor: Jeannette Martello, 800 S. Fairmount Ave., Suite 205, Pasadena, CA (US) 91105

( * ) Notice: Subject to any disclaimer, the term of this patent is extended or adjusted under 35 U.S.C. 154(b) by 0 days.

This patent is subject to a terminal disclaimer.

(21) Appl. No.: 10/654,958

(22) Filed: Sep. 5, 2003

(65) Prior Publication Data
US 2004/0230196 A1 Nov. 18, 2004

Related U.S. Application Data

(60) Division of application No. 09/747,991, filed on Dec. 27, 2000, now Pat. No. 6,648,892, which is a continuation of application No. 09/089,231, filed on Jun. 2, 1998, now Pat. No. 6,168,598.

(60) Provisional application No. 60/048,284, filed on Jun. 2, 1997.

(51) Int. Cl.
A61B 17/56 (2006.01)
A61B 17/04 (2006.01)
(52) U.S. Cl. .......................... 606/73; 606/232
(58) Field of Classification Search ................ 606/232, 606/73, 72, 104; 623/13.14
See application file for complete search history.

(56) References Cited

U.S. PATENT DOCUMENTS

| | | | | |
|---|---|---|---|---|
| 3,579,831 A * | 5/1971 | Stevens et al. | ............. | 433/174 |
| 4,870,957 A * | 10/1989 | Goble et al. | ................... | 606/73 |
| 4,988,351 A * | 1/1991 | Paulos et al. | ................. | 606/72 |
| 5,370,662 A * | 12/1994 | Stone et al. | ................ | 606/232 |
| 5,443,482 A * | 8/1995 | Stone et al. | ................ | 606/232 |
| 5,522,843 A * | 6/1996 | Zang | .......................... | 606/232 |
| 5,534,011 A * | 7/1996 | Greene et al. | .............. | 606/232 |
| 5,676,665 A * | 10/1997 | Bryan | .......................... | 606/61 |
| 5,778,623 A * | 7/1998 | Powell | ........................ | 52/410 |
| 5,782,865 A * | 7/1998 | Grotz | .......................... | 606/232 |
| 6,027,523 A * | 2/2000 | Schmieding | ................ | 606/232 |
| 6,319,270 B1 * | 11/2001 | Grafton et al. | ............. | 606/232 |

* cited by examiner

Primary Examiner—Pedro Philogene
(74) Attorney, Agent, or Firm—Terry M. Gernstein

(57) ABSTRACT

A surgical anchor is provided with one or more anchor holes distributed around the head of the anchor. Each anchor hole is inclined to allow attachment of one or more sutures to the anchor either before, during or after the anchor is seated in a bone. The upper and lower apertures of each anchor hole are chamfered, and the chamfered areas from the anchor hole to the outside edge shall be polished or somehow smoothed to remove sharp edges and rough areas which may cause friction and abrasion to soft tissue or suture material. The lower surface of the anchor head may be angled to further simplify the task of feeding a surgical needle through the anchor hole after the anchor is seated into the bone.

12 Claims, 5 Drawing Sheets

SOFT TISSUE SECURING ANCHOR

RELATED APPLICATIONS

This invention claims priority of copending U.S. provisional patent application Ser. No. 60/048,284. This is a divisional application of Ser. No. 09/747,991 filed on Dec. 27, 2000 now U.S. Pat. No. 6,648,892 which is a continuation of Ser. No. 09/089,231, filed on Jun. 2, 1998, now U.S. Pat. No. 6,168,598 which claimed the just-mentioned priority.

BACKGROUND OF THE INVENTION

1. Field of the Invention

The present invention relates generally to the field of surgical devices. In particular, this invention relates to anchors for attaching soft tissue to bone, and or to other soft tissue.

2. Background of the Invention

There are a number of conventional devices currently being marketed as anchors for securing soft tissue to bone. These devices have found application in surgical repair procedures throughout the human body. The conventional devices have some disadvantages which render them less than optimal for use in many operative procedures.

Conventional devices are generally metal, plastic or absorbable anchors which are screwed or press fit into pre-drilled holes in a bone. The conventional anchors have a suture-securing hole transverse to the long axis of the anchor. The suture-securing hole is generally located in the shank of the anchor which is therefore at or near the surface of the bone when the anchor is properly seated in the bone. The orientation of the suture securing hole in conventional anchors typically requires that the anchor have the suture threaded through the suture-securing hole, before the anchor is secured to the bone. A surgeon has little or no choice of the angle or position of tissue approximation, that is of attachment, when using such conventional anchors. Once a conventional anchor is secured in place, a surgeon is generally not able to rethread a suture through the suture-securing hole if the suture should break or otherwise come louse. Usually, a new anchor kit needs to be opened if the suture breaks. This leads to the inefficient use of the patient's operative time as well as the surgeon's time. Conventional anchors also only accommodate one suture per anchor and surgeons have little or no choice of suture material to be used with a particular anchor since the anchor kits are pre-loaded or come with a specific suture type.

Such conventional anchors require a surgeon to follow many steps and use special tools to successfully load and use the conventional anchors. First, the surgeon must gather the special tools necessary to use the conventional anchor. Second, the surgeon must thread the suture provided with the conventional anchor using a specialized threading tool. Third, the surgeon must drill an anchor hole into the bone which will secure the conventional anchor. Fourth, the surgeon must attach a conventional anchor to a special insertion tool. Fifth, the surgeon must secure the conventional anchor into the hole prepared in step three. Sixth, the surgeon must apply an appropriate surgical needle to an end of the free suture. Seventh, the surgeon must approximate the soft tissue to the conventional anchor using the needle and suture.

SUMMARY OF THE INVENTION

In accordance with the present invention, a soft tissue securing anchor is provided with one or more anchor holes distributed around the perimeter of the head of the anchor in a variety of orientations.

A soft tissue securing anchor according to the present invention may be used to secure soft tissue to bone, or to reapproximate a plurality of soft tissue points to a single bone site or to approximate soft tissue to soft tissue. The materials from which a soft tissue securing anchor are fabricated may be the same as conventional anchors, i.e. an inert material. Specific materials that may be used include plastic, stainless steel, titanium alloys, or absorbable materials. Thus a soft tissue securing anchor according to the present invention has the same effect on a body in which it is surgically secured as conventional anchors. Additionally, all types of conventional absorbable or non-absorbable sutures may be used with the present invention.

In a first aspect of the present invention, the anchor holes are inclined so that with the soft tissue securing anchor seated in the bone, the upper and lower apertures of each anchor hole are accessible to attach separate sutures to each of the anchor holes using conventional surgical techniques, i.e. curved needles. Any other variety of surgical needles may also be used. Additionally, free sutures, without attached needles may be threaded through these holes. The inclined anchor holes allow a surgeon to efficiently attach soft tissue to the soft tissue securing anchor using her preferred surgical tools without the necessity of using a multiplicity of specialized tools. Thereby making any given surgery more efficient and cutting down on costly operative time as well as time that the patient is exposed to potentially life-threatening anesthesia. The presence of a plurality of anchor holes in a single soft tissue securing anchor permits a surgeon to secure a plurality of soft tissue points with fewer soft tissue securing anchors than she would have been required using conventional anchors that only accommodate a single suture.

In another aspect of the present invention, the lower surface of the anchor head is angled relative to the long axis of the soft tissue securing anchor. The angle chosen is dictated by the surgeon's choice of needle and suture for a particular application. The angle of the lower surface of the anchor head combined with the angle of the anchor holes allows the surgeon to efficiently attach one or more sutures to a single soft tissue securing anchor. This minimizes the amount of foreign bodies that are surgically placed in a patient's body. Foreign body tissue reaction may lead to an increased rate of infection and, therefore, with the present invention, the patient would benefit with a lowered rate of foreign body tissue reaction. Additionally, since the suture to anchor body interface is very important with respect to operative stability, the possibility of now securing multiple soft tissue points to one anchor via the present invention means that if a single suture were to break, the operative approximation of soft tissue to bone or soft tissue to soft tissue would not be lost, as it is with the breaking of a suture attached to a conventional anchor.

In a further aspect of the present invention, each aperture of each anchor hole is chamfered to accommodate surgical needles. The chamfered aperture simplifies the surgeon's task of introducing the surgical needle into the anchor hole by widening the entry and exit apertures, and thus funneling the surgical needle point to the center of the anchor hole. The chamfer also lessens the angle of approximation the surgeon must achieve with a surgical needle to successfully pass the surgical needle and suture through the anchor hole. The chamfered areas, from the anchor hole to the outside edge, shall be polished or somehow smoothed to remove sharp edges and rough areas which may cause friction and abrasion of the tissue-approximating suture or the soft tissue itself. The chamfered aperture also minimizes acute edges in contact with the suture to minimize abrading of the suture thus allowing the liberal use of sliding knots on sutures passing through the present invention.

In a still further aspect of the present invention, an anchor for securing soft tissue to bone or soft tissue to soft tissue includes a conventional attachment means having a long axis and a head at a first end of the long axis, a means to accommodate a securing or drive tool, and an anchor hole through the head, the anchor hole has an upper aperture and a lower aperture. The anchor hole is oriented to cause a line through the center of the anchor hole to intersect an extension of the long axis beyond the head.

In a still further aspect of the present invention, an anchor for securing soft tissue to bone or soft tissue to soft tissue includes an attachment means having a long axis and a head at a first end of the long axis, a means to accommodate a securing or drive tool, and an anchor hole through the head, the anchor hole having an upper aperture and a lower aperture, the anchor hole oriented to cause a line through the center of the anchor hole to be skew to the long axis.

In another still further aspect of the present invention, a surgical anchor for reapproximating soft tissue to bone or soft tissue to soft tissue includes a screw having a head, a shank and a threaded end, a shoulder between the body and the shank to provide a visual and tactile reference for proper head height above the bone, a means to accommodate a securing or drive tool, and a plurality of generally radial anchor holes disposed about the circumference of the head and extending through the head, each anchor hole describing an angle between 0 and 75 degrees from the shank to a line through the anchor hole.

These and other features and advantages of this invention will become further apparent from the detailed description and accompanying figures that follow. In the figures and description, numerals indicate the various features of the invention, like numerals referring to like features throughout both the drawings and the description.

DETAILED DESCRIPTION OF THE PREFERRED EMBODIMENTS(S)

Figure 2:
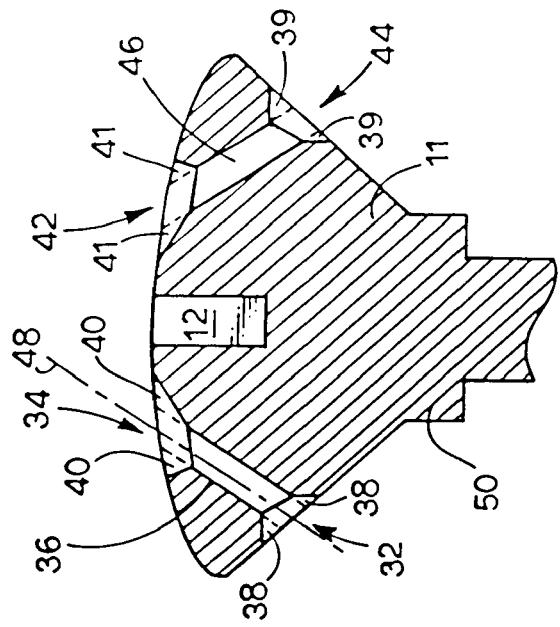
FIG. 2 is a cross sectional view of the head of the soft tissue securing anchor of FIG. 1 along A–A'.
Figure 1:
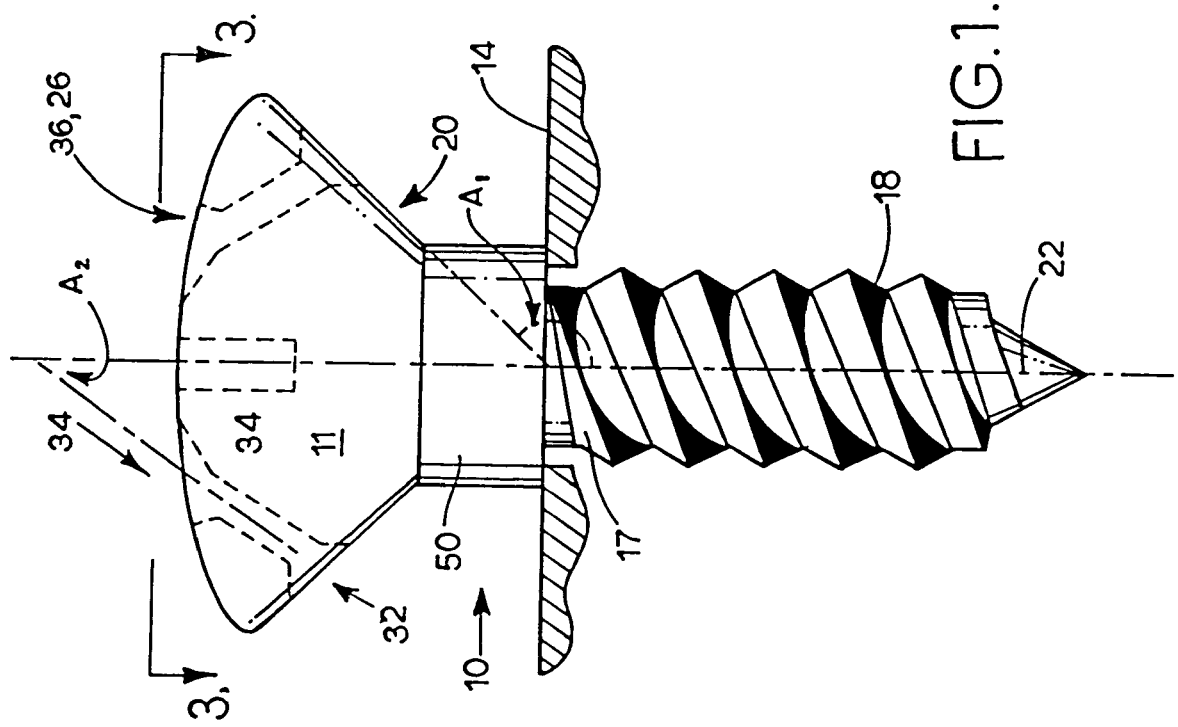
FIG. 1 is a side view of a soft tissue securing anchor according to the present invention.

Referring to FIG. 1, soft tissue securing anchor 10 includes head 11 and securing end 18. Securing end 18 may include any conventional means of securing a suture anchor into bone such as threads, barbs, fingers, toggle or molly bolts, and rivets. Suture anchor 10 may be secured into bone by any conventional means such as the application of torque or press-fit. The currently preferred embodiment of the present invention is a threaded, self tapping screw having a shoulder 50 which delineates head 11 from shank 17. Shoulder 50 provides a visual and physical indication to the surgeon to stop inserting soft tissue securing anchor 10 when shoulder 50 contacts bone 14. The size of shoulder 50 and the shape of head 11 are selected to permit access by surgical needle to both upper and lower apertures such as upper aperture 34 and lower aperture 32. Raising lower aperture 32 above bone 14 permits easy access to lower aperture 32. Head 11 may include a means for accommodating a drive tool such as a shaped head, tabs, flanges, channels, or one or more drive sockets such as drive socket 12 for securing anchor 10. A shaped head or drive socket such as drive socket 12 may be any conventional configuration compatible with surgical drive tools such as slotted, star, square, hex or allen shaped. Upper surface 16 of head 11 may be flat, convex or other conventional screw shape as shown in FIG. 2.

In accordance with one aspect of the present invention, lower surface 20 of head 11 may describe an angle $A_1$ between 90° and 150° from long axis 22. The angle of lower surface 20 may be determined by a surgeon's choice of needle and suture for a particular application. In the currently preferred embodiment of the present invention, the angle of lower surface 20 for a soft tissue securing anchor appropriate for cranial cosmetic surgery is about 40°–50° from long axis 22.

Figure 3:
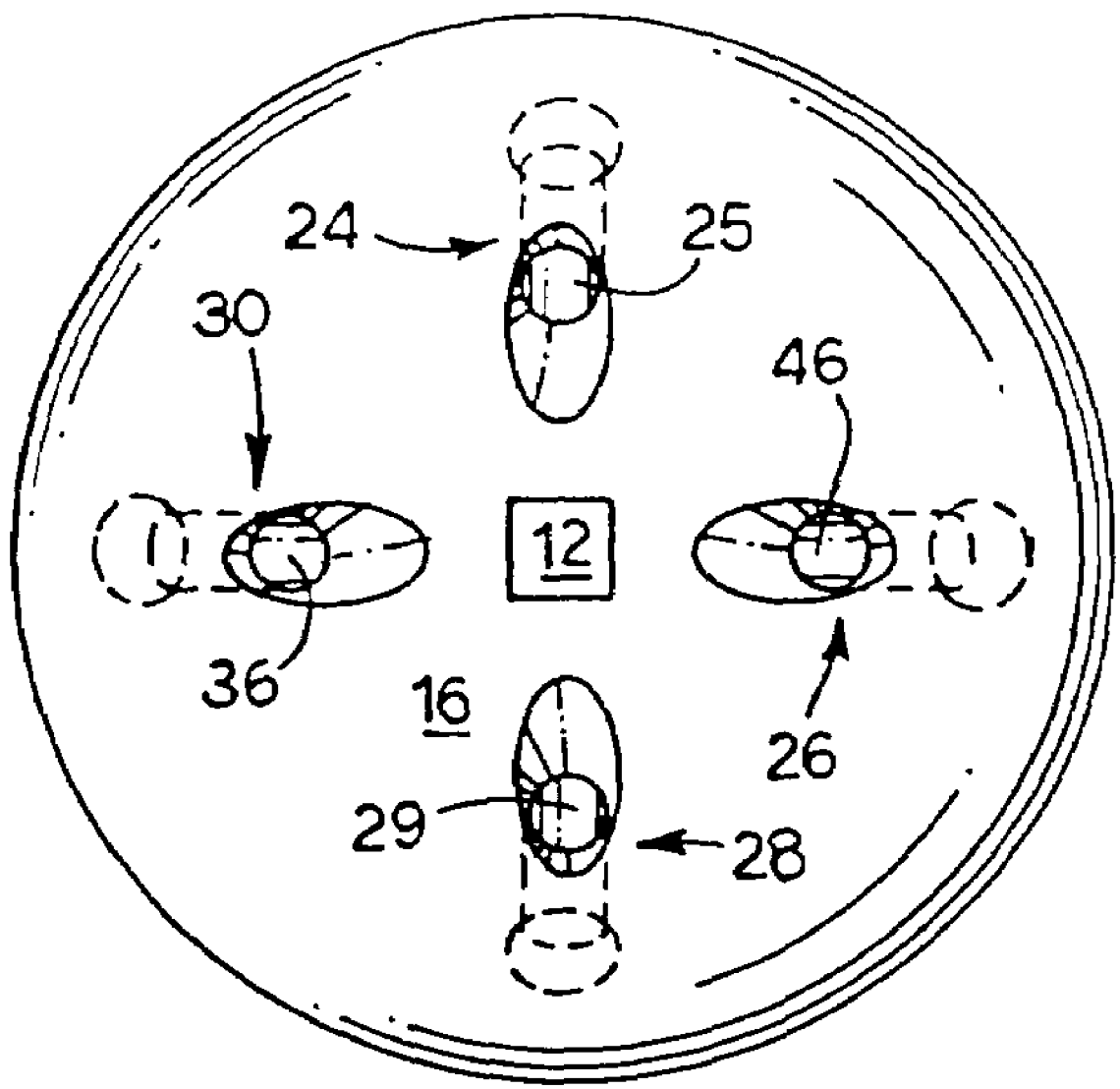
FIG. 3 is a top view of a soft tissue securing anchor according to the present invention.

Referring now to both FIGS. 1 and 3, soft tissue securing anchor 10 includes anchor points 24, 26, 28 and 30. Each anchor point has an upper aperture and a lower aperture. Anchor hale 36 includes upper aperture 34 and lower aperture 32. Anchor holes 25, 29, 36 and 46 may be inclined at an angle A: (or $A_2$ of FIG. 5B) between 0° and 75° from long axis 22. The angle of inclination, the diameter of the anchor holes, and the shape of head 11 are selected to accommodate the surgical task and a surgeon's choice of needle. The object is to secure the anchor, leaving sufficient space between lower aperture 32 and bone 14 for the surgeon to easily secure a suture through the anchor holes such as anchor hole 36. In a preferred embodiment of the present invention, soft tissue securing anchor 10 is appropriate for cranial cosmetic surgery and anchor holes 25, 29, 36 and 46 are inclined in the range of about 35°–50° from long axis 22.

In a further aspect of the present invention, each aperture of each anchor hole is chamfered to accommodate surgical needles. Referring now to FIG. 2, anchor hole 36 connects upper aperture 34 and lower aperture 32. Chamfer 38 widens lower aperture 32, and chamfer 40 widens upper aperture 34. In a preferred embodiment of the present invention appropriate for cranial cosmetic surgery, the chamfers 38 and 40 of anchor hole 36 are about 45° from center line 48. The chamfers may be cut to a depth of 5% to 50% of the total length of an anchor hole. In a preferred embodiment of the present invention, chamfers 38, 40, 39 and 41 are cut to 25% of the total length of anchor holes 36 and 46 respectively. Chamfers 38 and 39 shall be polished or somehow smoothed, from anchor hole 36 and 46 respectively to lower surface 20 to remove sharp edges and rough areas which may cause friction and abrasion of soft tissue or suture material. Chamfers 40 and 41 shall be polished or somehow smoothed, from anchor hole 36 and 46 respectively to upper surface 16 to remove sharp edges and rough areas which may cause friction and abrasion of soft tissue or suture material.

A preferred embodiment of the present invention is shown in FIGS. 1 and 3. Soft tissue securing anchor 10 is a stainless steel, pan-head, self-tapping screw having four anchor points 24, 26, 28 and 30 equally spaced around head 11. The preferred technique for using a soft tissue securing anchor according to the present invention is for the surgeon to expose bone 14 which will secure soft tissue securing anchor 10 using conventional surgical techniques. A hole is drilled into bone 14 by conventional means using either a hand or power drill. Soft tissue securing anchor 10 is screwed into bone 14 by applying a torque to soft tissue securing anchor 10 using a conventional surgical drive tool inserted into drive socket 12. When shoulder 50 contacts bone 14 soft tissue securing anchor 10 is seated. The surgeon may remove the drive tool from soft tissue securing anchor 10 and reapproximate soft tissue to the area of bone 14 which secures soft tissue securing anchor 10 by using conventional surgical techniques and sewing suture to anchor points 24, 26, 28 and 30.

In alternative techniques, sutures may be secured to anchor points 24, 26, 28 and 30 before, during or after the process of seating soft tissue securing anchor 10 in bone 14. These techniques are suited to bone sites which limit access to head 11 after soft tissue securing anchor 10 is seated. Thus the suture may be secured to soft tissue securing anchor 10 before, during or after soft tissue securing anchor 10 is fully seated into bone 14. This allows the surgeon to adopt her technique to a variety of securing sites for soft tissue securing anchors.

Figure 4A:
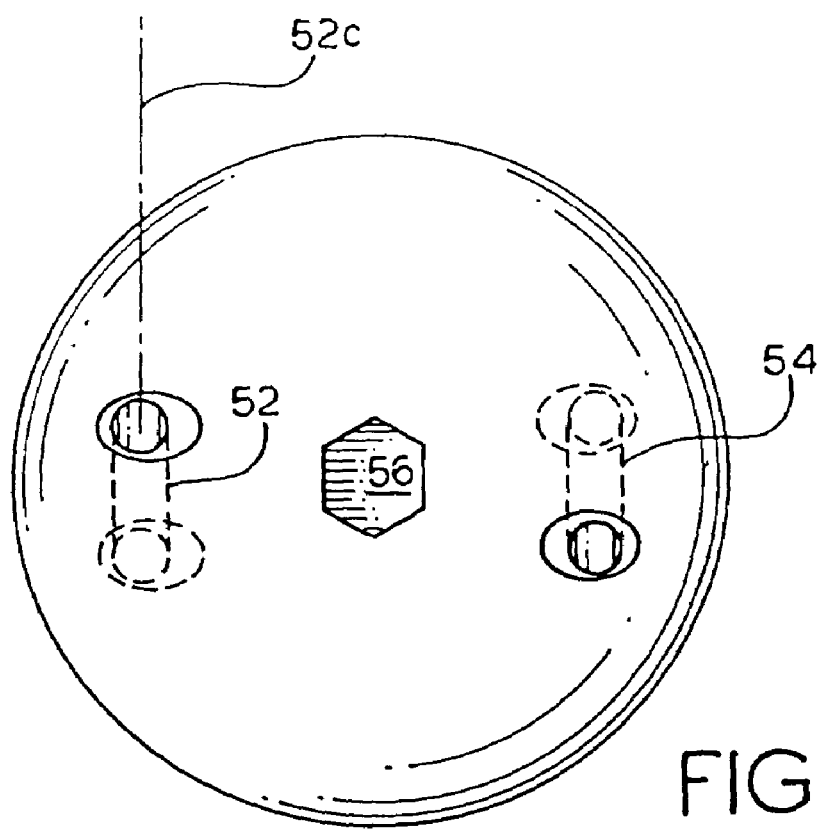
FIG. 4(a) is a top view of an alternate embodiment of a soft tissue securing anchor according to the present invention.
Figure 4B:
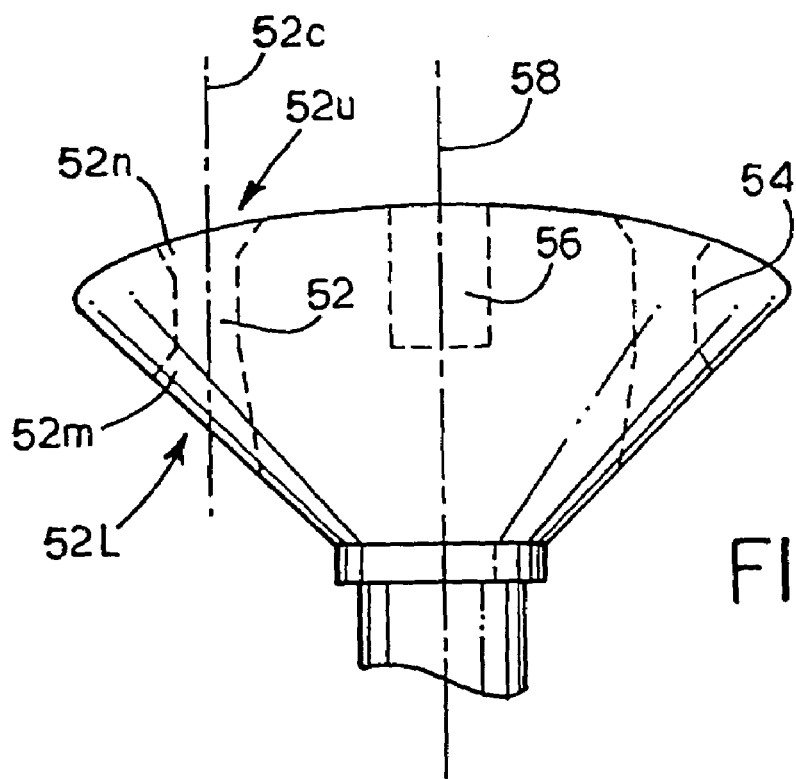
FIG. 4(b) is a side view of the soft tissue securing anchor of FIG. 4(a).

Referring now to FIGS. 4(*a*) and (*b*), an alternate embodiment of the present invention is shown in which anchor holes 52 and 54 are oriented skew to long axis 58. Each anchor hole has an upper aperture and a lower aperture. Anchor hole 52 includes upper aperture 52U and lower aperture 52L. Each aperture is chamfered. Upper aperture 52U includes aperture 52N. With anchor holes 52 and 54 oriented as shown in FIGS. 4(*a*) and (*b*), the angle formed between the anchor holes and a plane perpendicular to long axis 58 may be from 0° to 90°.

Figure 5A:
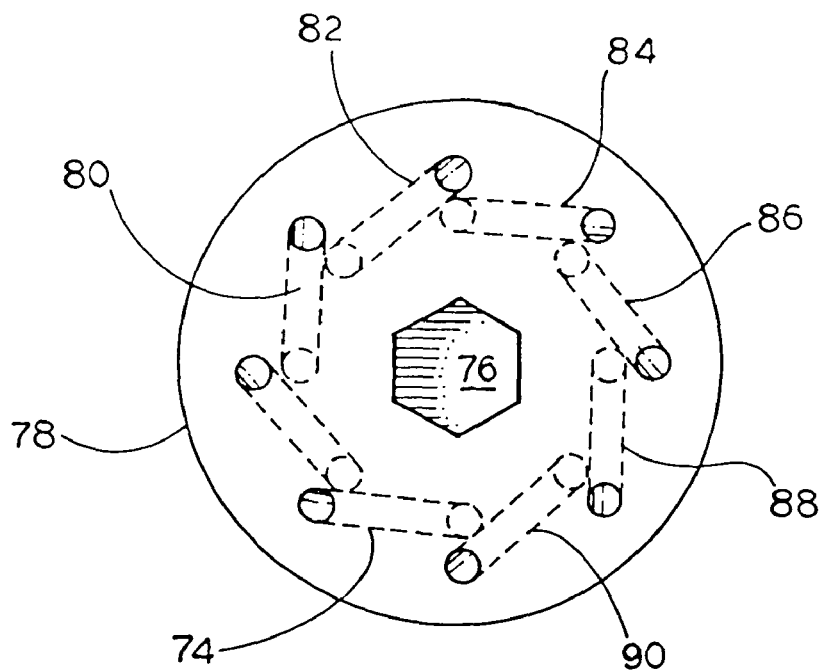
FIG. 5(a) is a top view of an alternate embodiment of a soft tissue securing anchor according to the present invention.
Figure 5B:
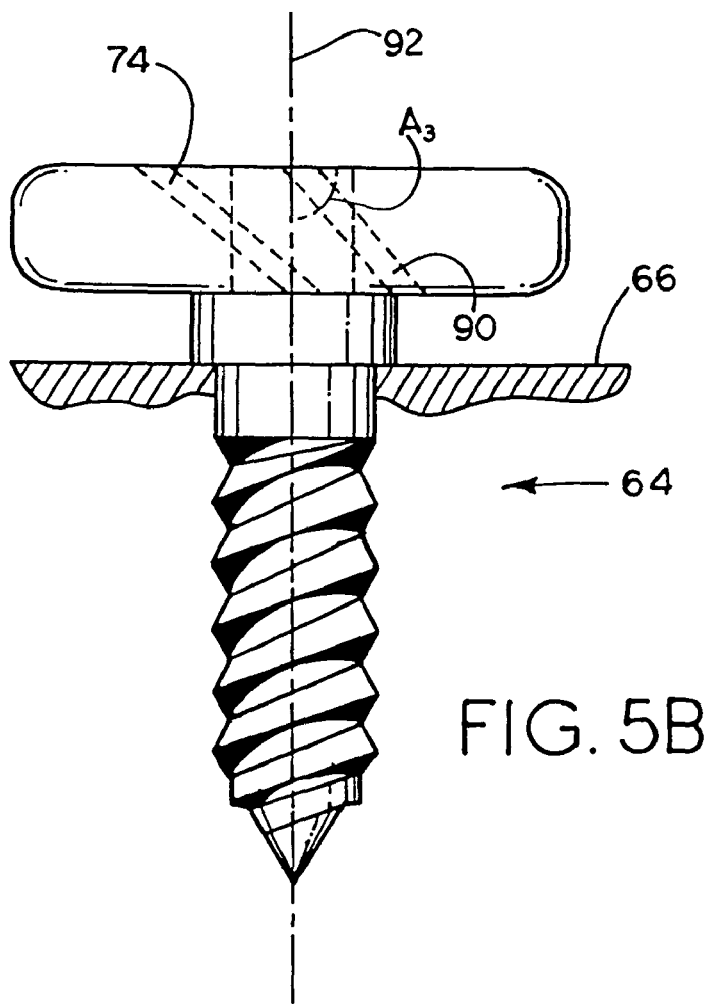
FIG. 5(b) is a side view of the soft tissue securing anchor of FIG. 5(a).

Referring now to FIGS. 5(*a*) and (*b*), an alternate embodiment of the present invention is shown in which lower surface 20 Anchor holes 74, 78, 80, 82, 84, 86, 88 and 90 are oriented generally parallel to drive socket 76. In FIG. 5(*b*) only anchor holes 74 and 90 are shown for clarity. With anchor holes 74 and 90 oriented as shown in FIGS. 5(*a*) and (*b*), the angle formed between the anchor holes and a plane perpendicular to long axis 92 may be from 0° to 90°.

Figure 6A:
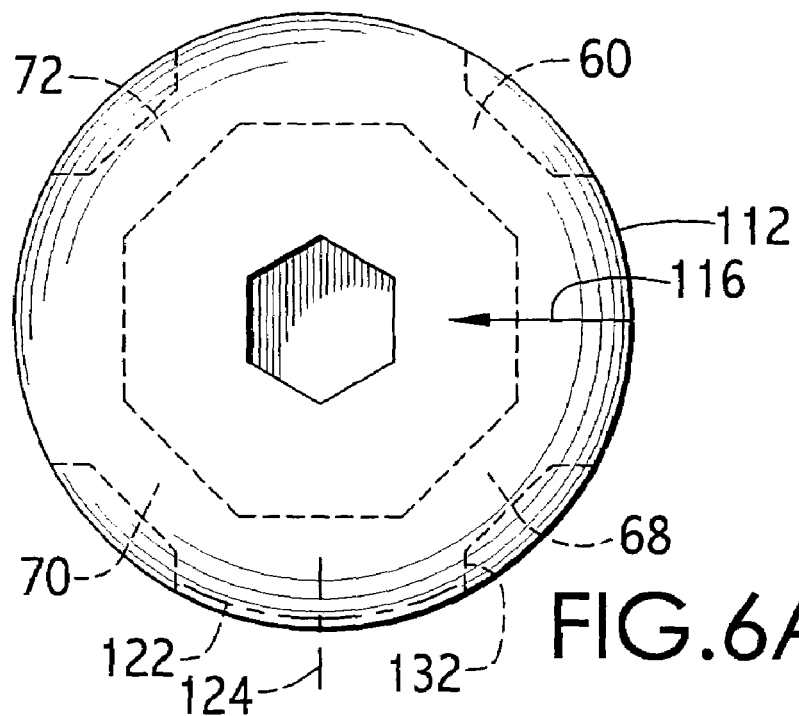
FIG. 6(a) is a top view of an alternate embodiment of a soft tissue securing anchor according to the present invention.
Figure 6B:
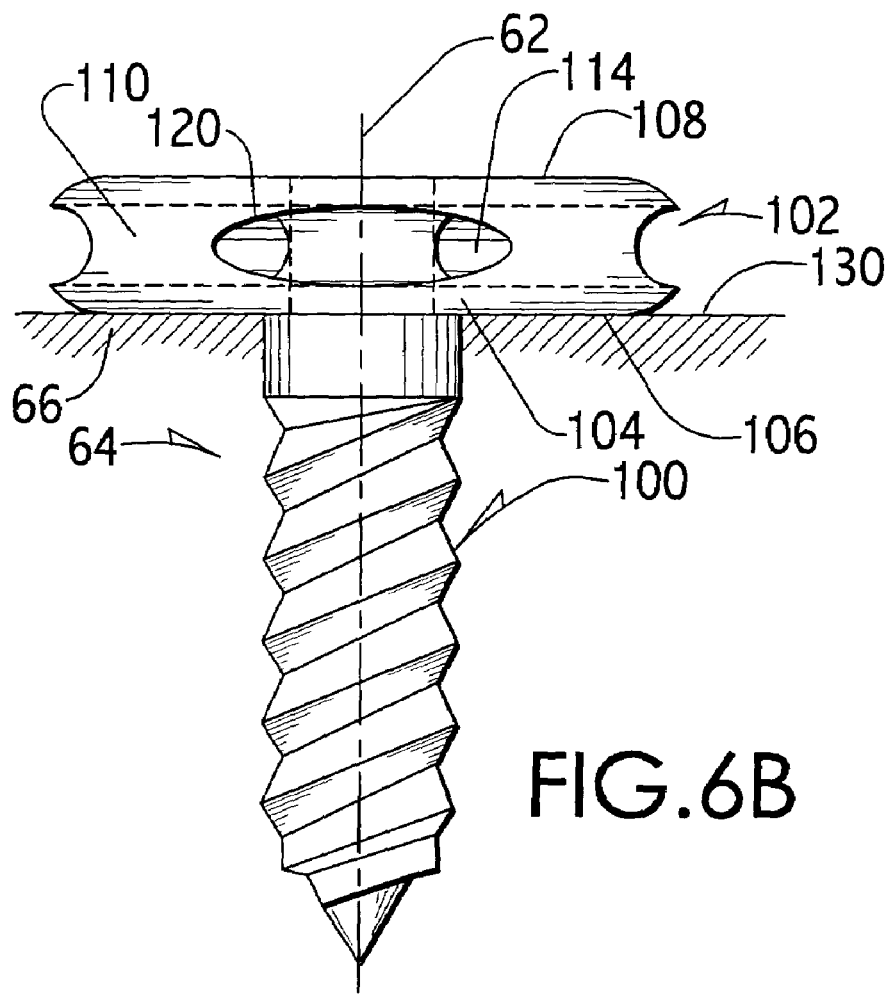
FIG. 6(b) is a side view of the soft tissue securing anchor of FIG. 6(a).

Referring now to FIGS. 6(*a*) and (*b*), anchor holes 60, 68, 70 and 72 form an angle of 0° with a plane perpendicular to long axis 62. The embodiment of the present invention shown in FIGS. 6(*a*) and (*b*) allows a surgeon to obtain an adequate angle of approximation to successfully secure one or more sutures to soft tissue anchor 64 by maintaining the surgical needle with the plane of its curve parallel to the surface of bone 66 as the surgical needle is passed through anchor hole 60, 68, 70 or 72 of soft tissue securing anchor 64. This embodiment of the present invention also presents a low profile above the surface of the bone in which it is secured.

As can also be understood from FIGS. 6(*a*) and (*b*), the surgical anchor shown in these figures comprises an anchor body 100 which has long axis 62. A head 102 is located at a first end 104 of the anchor body. The head is adapted to accommodate a tool for securing or driving the anchor body into a patient's bone. The head has a first surface 106 which is adapted to engage the patient's bone 66 when the anchor body is in place in the patient's bone. The head also has a second surface 108 that is adapted to be spaced apart from the patient's bone in the direction of the long axis of the anchor body when the anchor body is in place in the patient's bone. A side wall 110 connects the first surface of the head to the second surface of the head. The side wall defines an arcuate outer perimeter 112 of the head. The outer perimeter has an inside area 114 which is circumscribed by the outer perimeter and which is located inside the outer perimeter. As can be understood from FIG. 6(*a*), the tool will be accommodated in the inside area of the outer perimeter. The head has an inward direction 116 which extends from the outer perimeter of the head into the inside area of the outer perimeter.

As can be understood from FIGS. 6(*a*) and (*b*), the anchor includes a plurality of suture-accommodating apertures, such as suture-accommodating aperture 120, defined through the side wall. As can be seen in FIG. 6(*a*), the suture-accommodating apertures are spaced apart from each other around the outer perimeter of the head. Each suture-accommodating aperture has a transverse axis 122 which extends around the outer perimeter of the head and a longitudinal axis 124 which is oriented at a non-zero angle with respect to the transverse axis and which extends in the inward direction of the head. Each suture-accommodating aperture is adapted to be oriented parallel to a plane 130 containing the surface of the patient's bone against which the second surface of said head is enpageable when the anchor body is in place in the patient's bone. As is also shown in FIG. 6A, each passage also includes at least one chamfer. such as chamfer 132.

Having now described the invention in accordance with the requirements of the patent statutes, those skilled in this art will understand how to make changes and modifications in the present invention to meet their specific requirements or conditions.

What is claimed is:

1. A surgical anchor comprising:
   a threaded anchor body having a long axis and an outer dimension;
   a head at a first end of the anchor body adapted to accommodate a tool for securing or driving the anchor body into the bone of a patient, said head having an outer dimension that is greater than the outer dimension of said anchor body so said head is adapted to rest on the surface of the patient's bone when said anchor body is engaged in the bone and is located above the patient's bone when the anchor body is engaged in the bone, said head further including a first outer surface oriented to extend in the direction of the surface of the bone of the patient and a second outer surface that is oriented to extend in the direction of the surface of the bone of the patient, with the first outer surface abutting the surface of the patient's bone when the anchor body is in place and being located closer to the surface of the patient's bone than the second outer surface; and at least two suture passages extending through said head for receiving sutures, each passage having a longitudinal axis that is oriented at an oblique angle to the long axis of said anchor body and at an oblique angle to a plane containing the first outer surface of the head, the suture passages being oriented so that an extension of the longitudinal axis of each suture passage will not intersect the long axis of said threaded body, each of said suture passages having a first portion and a second portion, the first portion of each suture passage being located near the surface of the patient's bone and the second portion of each suture passage being located spaced apart from and above the surface of the patient's bone and each suture passage being located above the surface of the patient's bone when said anchor body is engaged in the patient's bone.

2. The surgical anchor defined in claim 1, wherein the head has an upper surface, at least a portion of each suture passage extending to the upper surface of the head.

3. The surgical screw anchor defined in claim 1 wherein adjacent passages are parallel to each other.

4. The surgical screw anchor defined in claim 3 wherein the passages are oriented in a circular pattern with respect to the long axis of said anchor body.

5. A surgical anchor comprising:
a threaded anchor body having a long axis, the anchor body having an outer dimension;
a first end of said anchor body adapted to accommodate a tool for attaching said anchor body to bone of a patient, said first end having an outer surface which abuts the bone of a patient when the anchor body is attached to the bone of the patient, the first end further including an outer dimension, the outer dimension of said first end being greater than the outer dimension of said anchor body so said first end rests on the surface of a patient's bone when said anchor body is engaged in the bone; and
at least one suture-accommodating passage defined in said first end to be located spaced from and above the surface of the bone and any tissue associated with the bone when said threaded anchor body is mounted in the bone to accept a suture thereinto and therethrough after said anchor body has been attached to the bone, said suture-accommodating passage being radially spaced apart from the long axis of said threaded anchor body and having a portion thereof located near the outer dimension of said anchor body and having a first end located adjacent to the patient's bone and a second end spaced apart from the first end and above the patient's bone when said anchor body is engaged in the patient's bone said suture-accommodating passage being oriented to be at an oblique angle to a plane containing the outer surface of the first end and so that neither the suture-accommodating passage nor an extension of the suture-accommodating passage intersects the long axis of said threaded anchor body, the second end of said suture-accommodating passage being spaced farther from the patient's bone than the first end of said suture-accommodating passage when said anchor body is engaged in the patient's bone.

6. The surgical anchor defined in claim 5 further including means on said anchor body for signaling when said anchor body is suitably fixed to the bone.

7. A surgical screw anchor unit fixedly securing soft tissue of a patient to bone of the patient comprising:

a needle;
a suture being fixedly secured to soft tissue of a patient and attached to the needle;
a one-piece threaded anchor body having a long axis and an outer dimension, the anchor body being fixedly secured to bone of the patient;
a head at a first end of the anchor body, the head being one piece with the anchor body and having an outer dimension that is larger than the outer dimension of the anchor body so the head rests on the surface of the bone of the patient, the head being located above the surface of the patient's bone; and
a plurality of passages through the head, the suture passing through one suture passage and being fixedly secured to the head to fixedly secure the soft tissue to the anchor body and via the anchor body fixedly to the bone of the patient, each suture passage having a longitudinal axis that is oriented at an angle with respect to the long axis of the anchor body, the longitudinal axis of each passage being oriented so that neither the longitudinal axis nor an extension of the longitudinal axis of each suture passage intersects the long axis of the anchor body, the suture passages being located above the surface of the patient's bone, each passage having a first end and a second end and having the first end located adjacent to the patient's bone and the second end located spaced above the patient's bone with the second end spaced farther from the patient's bone than the first end of each suture passage.

8. A surgical anchor unit fixedly securing soft tissue of a patient to bone of the patient comprising:
a needle;
a suture attached to the needle and being fixedly secured to soft tissue of a patient;
a one-piece threaded screw having a head, a shank and a threaded end, the head and the shank and the threaded end all being one piece with each other, the head having an arcuate outer dimension with a center, the shank having an outer dimension and a long axis which is located near the center of the outer dimension of the head, with the outer dimension of the head being greater than the outer dimension of the shank so the head rests on the surface of a patient's bone and is located above the surface of the patient's bone;
the head including a plurality of anchor holes each extending through the head at an oblique angle with respect to the long axis of the shank for receiving a suture, the anchor holes being located near the outer dimension of the head and radially spaced apart from the long axis of the shank and being located above the surface of the patient's bone, each anchor hole being oriented so that neither the anchor hole nor an extension of the anchor hole intersects the long axis of the shank, each anchor hole having a first end and a second end, the second end of each anchor hole being spaced farther from the patient's bone than the first end of the anchor hole, the suture being fixedly secured to soft tissue extending through an anchor hole and fixedly secured to the screw and fixedly securing the soft tissue being fixedly secured thereto to the patient's bone via the one-piece screw.

9. A surgical screw anchor unit comprising:
a needle;
a suture being fixedly secured to soft tissue of a patient and attached to the needle;

a threaded anchor body with a pointed first end, a second end and a body axis extending through the ends, the anchor body being fixedly secured to bone of the patient;

a head located at the anchor body outer end, the head having an outer surface that extends in a direction of the surface of the patient's bone;

a suture passage extending through the head and having first and second apertures and a bore connecting the first and second apertures, the second aperture being located farther away from the surface of the patient's bone than the first aperture;

the suture extending through the suture passage and being fixedly secured to the anchor body, the soft tissue fixedly secured to the suture being fixedly secured to the patient's bone via the fixed securing of the suture to the anchor body which is adapted to be fixedly secured to the patient's bone;

the suture passage opening onto the outer surface of the head at the apertures; and the suture passage being oriented with respect to the body axis to extend in a direction of the body axis with one of the apertures positioned closer to the bone of the patient than the other aperture, the suture passage being oriented so that neither the suture passage nor an extension of the suture passage intersects the body axis.

10. A surgical screw anchor unit fixedly securing soft tissue of a patient to a bone of the patient comprising:

a needle;

a suture attached to the needle and being fixedly attached to soft tissue of a patient;

a threaded anchor body with a pointed first end, a second end and a body axis extending through the ends, the anchor body being fixedly secured to bone of the patient;

a head located at the anchor body second end and having an outer surface that is oriented to extend in the direction of a surface of the patient's bone;

a suture passage extending through the head and having first and second apertures;

the suture passing through the suture passage and being fixedly attached to the anchor body, the soft tissue being fixedly secured to the patient's bone via the suture being fixedly attached to the soft tissue and to the anchor body;

the suture passage opening onto the outer surface of the head at the apertures; and the suture passage being oriented at a non-right angle to the body axis of the threaded anchor body, the first aperture of the passage being located closer to the surface of the patient's bone than the second aperture, the suture passage being oriented so that neither the suture passage nor an extension of the suture passage intersects the body axis.

11. A surgical screw anchor unit comprising:

a suture being fixedly secured to soft tissue of a patient;

a threaded anchor body having a long axis and an outer dimension, the anchor body being fixedly secured to bone of a patient;

a head at a first end of the anchor body, the head having an outer dimension that is larger than the outer dimension of the anchor body; and a plurality of suture passages through the head, each suture passage having a first end and a second end and longitudinal axis that extends between the first end of the suture passage and the second end of the suture passage and which is oriented at an angle with respect to the long axis of the anchor body, each suture passage being spaced apart from the long axis of the anchor body and oriented so that neither the suture passage nor an extension of the suture passage intersects the long axis of the anchor body, the second end of each suture passage being spaced farther from the patient's bone than the first end of the suture passage, the suture extending through a suture passage and being fixedly attached to the anchor body, the soft tissue being fixedly secured to the suture being fixedly secured to the bone of the patient via the suture being fixedly secured to the soft tissue and to the anchor body which is adapted to be fixedly secured to the bone of the patient.

12. A surgical screw anchor unit comprising:

a suture being fixedly secured to soft tissue of a patient;

a threaded anchor body having a long axis and an outer dimension, the anchor body being fixedly secured to bone of a patient;

a head at a first end of the anchor body; and a suture passage through the head, the suture passage having a first end and a second end and longitudinal axis that extends between the first end of the suture passage and the second end of the suture passage and which is oriented at an angle with respect to the long axis of the anchor body, the suture passage being spaced apart from the long axis of the anchor body and oriented so that neither the suture passage nor an extension of the suture passage intersects the long axis of the anchor body, the second end of the suture passage being spaced farther from the patient's bone than the first end of the suture passage, the suture extending through the suture passage and being fixedly attached to the anchor body, the soft tissue being fixedly secured to the suture being fixedly secured to the bone of the patient via the suture being fixedly secured to the soft tissue and to the anchor body which is adapted to be fixedly secured to the bone of the patient.

* * * * *